US006719922B1

(12) United States Patent
Reinehr et al.

(10) Patent No.: US 6,719,922 B1
(45) Date of Patent: Apr. 13, 2004

(54) MIXTURES OF FLUORESCENT WHITENING AGENTS

(75) Inventors: Dieter Reinehr, Kandern (DE); Hanspeter Sauter, Schopfheim (DE); Hans Kramer, Frick (CH); Werner Schreiber, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/070,631

(22) PCT Filed: Aug. 29, 2000

(86) PCT No.: PCT/EP00/08403

§ 371 (c)(1),
(2), (4) Date: Jul. 8, 2002

(87) PCT Pub. No.: WO01/18301

PCT Pub. Date: Mar. 15, 2001

(30) Foreign Application Priority Data

Sep. 6, 1999 (EP) ........................................... 99810799

(51) Int. Cl.[7] ............................. D06L 3/12; C11D 3/42

(52) U.S. Cl. .......................... 252/301.21; 8/922; 8/648

(58) Field of Search ....................... 252/301.21, 301.22; 8/922, 648

(56) References Cited

U.S. PATENT DOCUMENTS 4,380,514 A * 4/1983 Seybold ...................... 558/373
5,695,686 A * 12/1997 Hauptreif et al. ...... 252/301.21
6,482,241 B1 * 11/2002 Metzger et al. ............ 8/115.51

FOREIGN PATENT DOCUMENTS

| | | | |
|---|---|---|---|
| DE | 19609956 | | 9/1996 |
| EP | 0023027 | | 1/1981 |
| EP | 0719356 | | 4/1998 |
| GB | 2200660 | | 8/1988 |
| GB | 2200660 A | * | 8/1988 |

* cited by examiner

*Primary Examiner*—C. Melissa Koslow
(74) *Attorney, Agent, or Firm*—Kevin T. Mansfield

(57) ABSTRACT

The present invention relates to a mixture of fluorescent whitening agents comprising 20 to 70% by weight of a compound of formula (1), 30 to 80% of a compound of formula (2) and 0.5 to 5% of a compound of formula (3), compositions containing the mixture and the use of the compositions for whitening synthetic fibers, in particular polyester.

(1)

CN CN (2)

CN CN (3)

NC CN

7 Claims, No Drawings

MIXTURES OF FLUORESCENT WHITENING AGENTS

The present invention relates to mixtures of fluorescent whitening agents based on various isomers of cyano-substituted 1,4-bis-styrylbenzenes.

Fluorescent whitening agents are often used in the form of mixtures of two or more components, since such mixtures may exhibit a higher degree of whiteness than that of the sum of the individual components alone.

Thus, for example, GB 2200660 describes such mixtures although the composition is restricted by the method of preparation, whilst U.S. Pat. No. 5,695,686 describes similar asymmetric mixtures containing further isomers again due to the process of preparation. Furthermore, DE 19609956 describes extremely complex mixtures containing up to five different isomers of the dicyano-substituted distyryl benzenes.

The constitution of such mixtures of the dicyano-substituted distyryl benzenes is important not only in regard to their whitening effects, but also with regard to the shade, which may be more or less reddish or greenish, the desirability being a matter of utmost importance to the end user.

It has now, surprisingly, been found that particularly high degrees of whiteness in especially desirable shades are obtained from mixtures of fluorescent whitening agents comprising 20 to 70% by weight of a compound of formula

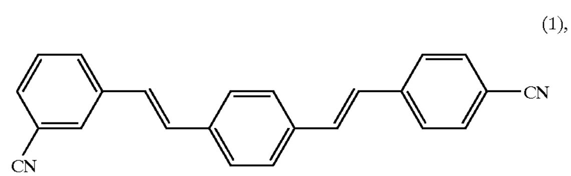

30 to 80% of a compound of formula

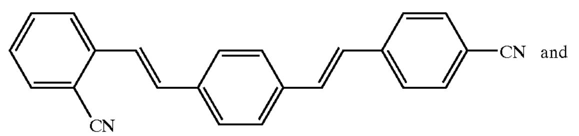

0.5 to 5% of a compound of formula

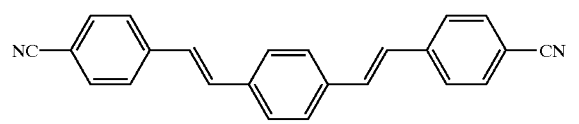

Furthermore, mixtures comprising 50 to 70% by weight of the compound of formula (1), 30 to 50% of the compound of formula (2) and 0.5 to 5% of the compound of formula (3) are of particular interest, whilst mixtures comprising 55 to 70% by weight of the compound of formula (1), 30 to 45% of the compound of formula (2) and 0.5 to 3% of the compound of formula (3) are especially suitable and, preferably, mixtures comprising 58 to 62% by weight of the compound of formula (1), 38 to 42% of the compound of formula (2) and 0.5 to 3% of the compound of formula (3) should be used.

The mixtures of the invention are prepared by condensing terephthalaldehyde with a 4-dialkylphosphonomethyl benzonitrile and further condensing the resulting 4 cyano-4'-formylstilbene obtained as intermediate with a 2- or 3-dialkylphosphonomethyl benzonitrile according to the following scheme:

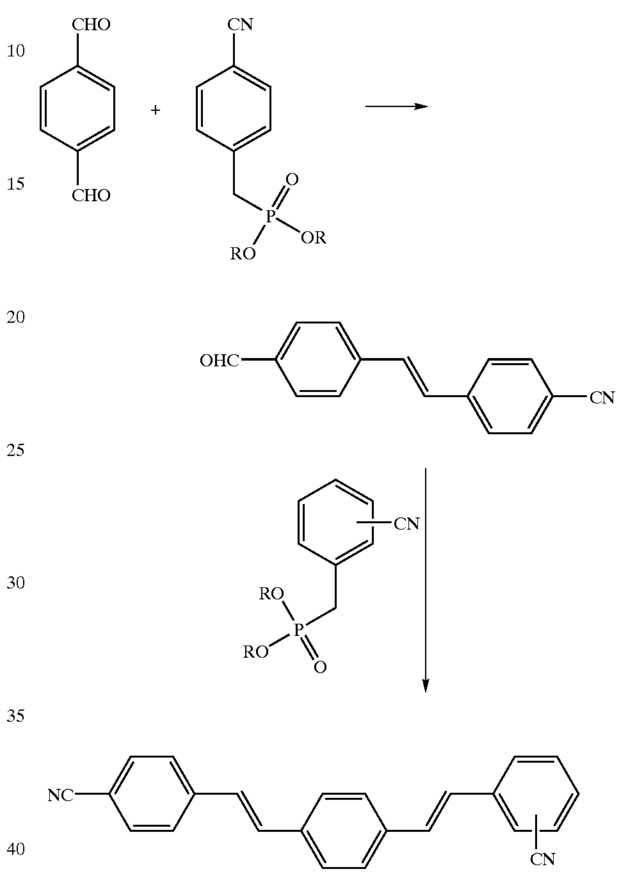

whereby R represents methyl, ethyl, propyl or butyl, preferably methyl or ethyl.

The initial condensation of terephthalaldehyde with a 4-dialkylphosphonomethyl benzonitrile is carried out in a lower alcohol, for example methanol, ethanol, n- or isopropanol or n-, sec.- or tert.-butanol, preferably methanol, as solvent and in the presence of an alkali metal hydroxide such as lithium, potassium or sodium hydroxide, preferably potassium hydroxide. During the course of this condensation, small amounts, i.e. up to 5%, of 4,4'-dicyano-(1,4-bis-styryl)benzene are produced as a by-product, which is then advantageously present in the final mixture. After reaction, the 4 cyano-4'-formylstilbene precipitates from the reaction mixture and is isolated by filtration.

The second condensation step is carried out in a dipolar aprotic solvent such as dimethyl-formamide, dimethyl sulphoxide, N-methyl pyrrolidone or tetramethyl urea, preferably dimethylformamide, in the presence of strong base such as a sodium or potassium $C_1$–$C_5$-alcoholate, especially sodium methylate.

Further objects of the present invention are the use of the mixtures of the three compounds of the formulae (1) to (3) for whitening synthetic fibres, in particular polyester fibres, said compositions containing a mixture comprising 20 to 70% by weight of a compound of formula (1),

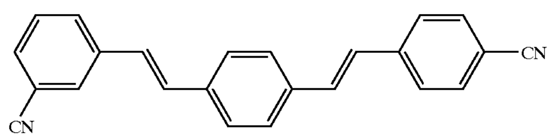

30 to 80% of a compound of formula (2)

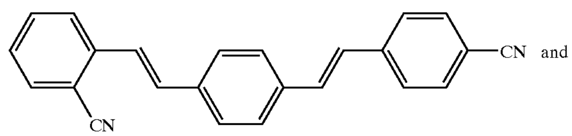

0.5 to 5% of a compound of formula (3).

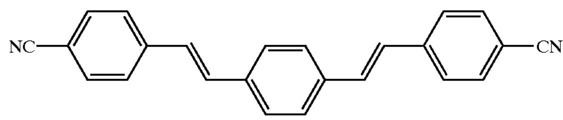

Furthermore, mixtures comprising 50 to 70% by weight of the compound of formula (1), 30 to 50% of the compound of formula (2) and 0.5 to 5% of the compound of formula (3) are of particular interest, whilst mixtures comprising 55 to 70% by weight of the compound of formula (1), 30 to 45% of the compound of formula (2) and 0.5 to 3% of the compound of formula (3) are especially suitable and, preferably, mixtures comprising 58 to 62% by weight of the compound of formula (1), 38 to 42% of the compound of formula (2) and 0.5 to 3% of the compound of formula (3) should be used.

As is customary with mixtures of fluorescent whitening agents, the individual components can be processed to the commercial form by dispersing them in a liquid medium, preferably water. This can be done by dispersing the individual components and then combining the dispersions so obtained. However, it is also possible to mix the individual components together in substance and then to disperse them jointly. The dispersing operation is carried out in a conventional manner in ball mills, colloid mills, bead mills or the like.

The present invention thus further provides brightener compositions containing water and, in each case based on the weight of the formulation, from 3 to 25% by weight, preferably from 5 to 15% by weight of the above defined fluorescent whitening agent mixture and also 0 to 60%, preferably 5 to 50% by weight, of auxiliaries.

Suitable auxiliaries include, for example, anionic or non-ionic dispersants from the class of ethylene oxide adducts with fatty alcohols, higher fatty acids or alkyl phenols or ethylenediamine ethylene oxide-propylene oxide adducts, copolymers of N-vinylpyrrolidone with 3-vinylpropionic acid, water retention aids, such as ethylene glycol, glycerol or sorbitol, or biocides.

The mixtures of this invention and the compositions containing them are suitable for whitening textile materials made from synthetic fibres, in particular, those made from linear polyesters. However, these mixtures and compositions can also be used for whitening blends that contain linear polyesters.

The mixtures of this invention are applied by the methods normally employed for the application of fluorescent whitening agents, for example, by the exhaust dying process in dying machines or by pad-thermofixation. The treatment is conveniently effected in an aqueous medium in which the compounds are present in finely particulate form as suspensions, microdispersions or, as the case may be, solutions. If appropriate, dispersants, stabilisers, wetting agents and other assistants can be added during the treatment. The treatment is normally carried out in the temperature range from about 20° C. to 140° C., preferably 110 to 130° C., for example, at the boiling temperature of the bath or in the proximity thereof. Where the mixtures are applied by the pad-thermofixation process, the thermofixing is preferably carried out at a temperature of between 170 and 200° C.

The following Examples serve to illustrate the invention; parts and percentages are by weight, unless otherwise stated.

A. PREPARATIVE EXAMPLES

Example1

4 Cyano-4'-formylstilbene

Under an atmosphere of nitrogen, a 1.5 l. flask is charged with 480 ml. of methanol and 43.4 g. of 85% potassium hydroxide powder are added with stirring. The potassium hydroxide dissolves and the temperature rises to 43° C. The solution is cooled to 2° C. and 82.1 g. of 98% terephthaldehyde added. To the resulting clear solution, a solution of 144.8 g. of 4-dimethylphosphonomethyl-benzonitrile in 120 ml. of methanol is added dropwise with stirring and cooling over 2 hours at 2° C. After stirring for 2 hours at 2° C., the temperature is raised to 25° C. and the mixture stirred for a further 2 hours. Subsequently, the temperature is raised to 40° C. and stirring continued for a further 2 hours at this temperature. The mixture is then diluted with 180 ml. of methanol and the suspension stirred at room temperature overnight. The precipitate is then filtered with suction, washed with 250 ml. of methanol and sucked dry. There are obtained 260 g. of moist filter cake, corresponding to 123 g. of a dry product containing 98.7% of 4 Cyano-4'-formylstilbene and 1.3% 4,4'-dicyano-(1,4-bis-styryl) benzene of formula (3).

Example 2

(1),

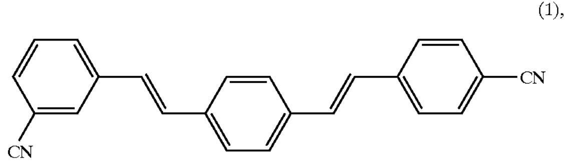

Under an atmosphere of nitrogen, a 1.5 l. flask is charged with 380 ml. of N,N-dimethyl-formamide and 131.8 g. of 3-dimethylphosphonomethyl-benzonitrile and 259.0 g. of moist filter cake obtained in Example 1 added successively. The yellow suspension is warmed to 40° C. and 99.0 g. of a 30% solution of sodium methylate in methanol added dropwise with cooling over 40 min. at 40 to 44° C. The resulting suspension is then stirred for a further 4 hours at 40 to 42° C. and then overnight at room temperature. After dilution with 400 ml. of methanol, the mixture is rendered neutral to phenolphthalein by the addition of 8.0 g. of formic acid, cooled to 0° C. and filtered. The filter cake is washed with 2 portions of 250 ml. of methanol. After drying at 70° C. under vacuum, there are obtained 137.8 g. of product containing 94.8% of the compound of formula (1) and 1.9% of the compound of formula (3).

Example 3

(2)

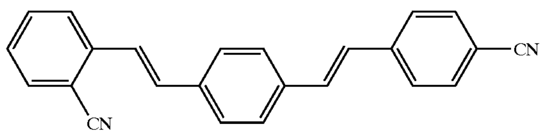

Under an atmosphere of nitrogen, a 1.5 l. flask is charged with 170 ml. of N,N-dimethyl-formamide and 331.2 g. of 34% 2-dimethylphosphonomethyl-benzonitrile and 272.0 g. of moist filter cake obtained in Example 1 added successively. The suspension is warmed to 40° C. and 99.0 g. of a 30% solution of sodium methylate in methanol added dropwise with cooling over 40 min. at 40 to 44° C. The resulting suspension is then stirred for a further 4 hours at 40 to 42° C. After dilution with 400 ml. of methanol, the mixture is stirred overnight at room temperature, rendered neutral to phenolphthalein by the addition of 4.0 g. of formic acid, cooled to 0° C. and filtered. The filter cake is washed with 2 portions of 250 ml. of methanol. After drying at 70° C. under vacuum, there are obtained 133.1 g. of a yellowish product containing 98.9% of the compound of formula (2) and 0.7% of the compound of formula (3).

B. APPLICATION EXAMPLES a) Exhaust Process

A polyester fabric (Terylene type 540) is treated, in a dyeing apparatus, at room temperature and at a liquor ratio of 1:20, with an aqueous bath containing 0.1% by weight of a mixture of the optical brightening agents of formula (1), (2) and (3) in the ratios given in Table 1, in finely dispersed form and in the presence of 1 g/l. of a fatty alcohol polyglycol ether as dispersing agent. The temperature is raised from room temperature to 110 over 30 minutes, held for a further 30 minutes at this temperature and subsequently cooled to 40° C. during 15 minutes. The textile material is then rinsed for 30 seconds under running water and dried at 70° C.

The so-treated polyester fabric exhibits a high degree of whiteness, as measured according to Ganz (see Table 1), with a neutral bluish shade.

b) Pad-thermofixation Process

A polyester fabric (Terylene type 540) is treated at room temperature by the pad-batch process with an aqueous liquor containing 1.2 g/l % of a mixture of the optical brightening agents of formula (1), (2) and (3) in the ratios given in Table 1, in dispersed form and in the presence of 1 g/l of an alkali salt of a sulfonated dicarboxylic acid alkyl ester. The pinch-off effect is 65%. Subsequently, the fabric sample is dried for 30 minutes at 70° C. and then thermofixed during 30 seconds at 180° C.

The so-treated polyester fabric exhibits a high degree of whiteness, as measured according to Ganz (see Table 1), with a neutral bluish shade.

TABLE 1

| Example | Compound (1) % | Compound (2) % | Compound (3) % | Whiteness Process a) | Whiteness Process b) |
|---|---|---|---|---|---|
| 4 | 63.75 | 34.75 | 1.5 | 211 | 216 |
| 5 | 63.0 | 34.5 | 2.5 | 211 | 215 |
| 6 | 62.5 | 34.0 | 3.5 | 210 | 216 |
| 7 | 58.75 | 37.75 | 1.5 | 208 | 216 |
| 8 | 39.25 | 59.5 | 1.25 | 206 | 210 |
| 9 | 29.5 | 69.5 | 1.0 | 204 | 210 |
| 10 | 20.0 | 79.0 | 1.0 | 207 | 210 |

What is claimed is:

1. A mixture of fluorescent whitening agents comprising 55 to 70% by weight of a compound of formula (1),

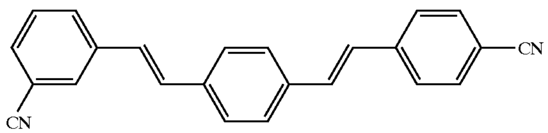

30 to 45% of a compound of formula (2)

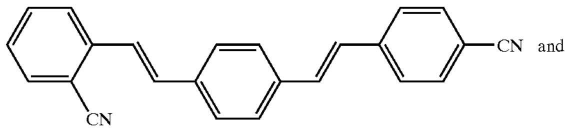

0.5 to 3% of a compound of formula (3).

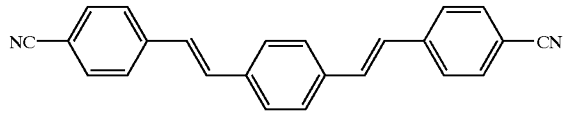

2. A mixture according to claim 1 comprising 58 to 62% by weight of the compound of formula (1), 38 to 42% of the compound of formula (2) and 0.5 to 3% of the compound of formula (3).

3. A composition for whitening synthetic fibres, which contains water, a mixture of fluorescent whitening agents according to claim 1 and, optionally, auxiliaries.

4. A composition for whitening synthetic fibres according to claim 3 containing water and, in each case based on the weight of the formulation, from 3 to 25% by weight of the fluorescent whitening agent mixture and also 0 to 60% of auxiliaries.

5. A composition for whitening synthetic fibres according to claim 3 containing water and, in each case based on the weight of the formulation, from 5 to 15% by weight of the fluorescent whitening agent mixture and also 5 to 50% of auxiliaries.

6. A method of whitening synthetic fibres which comprises treating said fibres with a mixture of fluorescent whitening agents comprising 20 to 55% by weight of a compound of formula

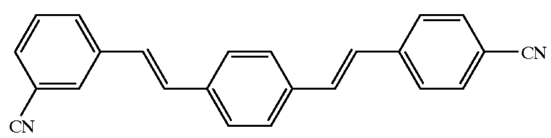
(1),
30 to 45% of a compound of formula
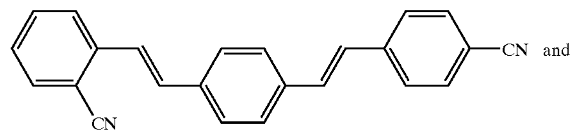
(2) and
0.5 to 3% of a compound of formula
(3).
7. A method according to claim 6 wherein the synthetic fibres are polyester fibres.
* * * * *